(12) United States Patent
Natori et al.

(10) Patent No.: US 8,304,452 B2
(45) Date of Patent: Nov. 6, 2012

(54) RADICAL SCAVENGER AND ACTIVE OXYGEN ELIMINATING AGENT

(75) Inventors: Shunji Natori, Kitasoma-gun (JP); Kunimiki Ootsu, Machida (JP); Hajime Okuyama, Nerima-ku (JP)

(73) Assignee: InBiotex Inc., Tokyo (JP)

( * ) Notice: Subject to any disclaimer, the term of this patent is extended or adjusted under 35 U.S.C. 154(b) by 0 days.

(21) Appl. No.: 12/986,376

(22) Filed: Jan. 7, 2011

(65) Prior Publication Data

US 2011/0212883 A1    Sep. 1, 2011

Related U.S. Application Data

(62) Division of application No. 11/916,942, filed as application No. PCT/JP2006/311269 on Jun. 6, 2006, now abandoned.

(30) Foreign Application Priority Data

Jun. 7, 2005    (JP) .................. 2005-166842

(51) Int. Cl.
*A01N 37/12* (2006.01)
*A01N 37/10* (2006.01)

(52) U.S. Cl. .................. 514/561; 514/562; 514/568

(58) Field of Classification Search .......... None
See application file for complete search history.

(56) References Cited

U.S. PATENT DOCUMENTS

| | | | |
|---|---|---|---|
| 3,883,674 A | 5/1975 | Ninagawa et al. | |
| 4,125,519 A | 11/1978 | Goodman et al. | |
| 4,863,457 A | 9/1989 | Lee | |
| 6,046,046 A | 4/2000 | Hassanein | |
| 7,488,749 B2 * | 2/2009 | Schraermeyer | 514/415 |

FOREIGN PATENT DOCUMENTS

| | | |
|---|---|---|
| JP | 49-43884 | 4/1974 |
| JP | 2-129101 | 5/1990 |
| JP | 8-337594 | 12/1996 |
| JP | 2000-515115 | 11/2000 |
| JP | 2001-213799 | 8/2001 |
| JP | 2001-226283 | 8/2001 |
| JP | 2001-516768 | 10/2001 |
| JP | 2002-173473 | 6/2002 |
| JP | 3586809 | 8/2004 |
| JP | 2005-8625 | 1/2005 |
| JP | 3634894 | 1/2005 |
| JP | 2005-213159 | 8/2005 |
| JP | 2005213159 | * 8/2005 |

(Continued)

OTHER PUBLICATIONS

Database CAPLUS Chemical Abstracts Service, Columbus, Ohio, US; Database Accession No. 2001:603499, Abstract of JP 2001226283.*

(Continued)

*Primary Examiner* — Karl J Puttlitz
(74) *Attorney, Agent, or Firm* — Oblon, Spivak, McClelland, Maier & Neustadt, L.L.P.

(57) ABSTRACT

It is an object to provide a radical scavenger, an active oxygen-scavenging agent and the like, which are highly efficacious clinically and novel, and so as to attain the object, 3,4-dihydroxyphenylalanine derivatives such as N-β-alanyl-5-S-glutathionyl-3,4-dihydroxyphenylalanine (5-S-GAD) or pharmaceutically acceptable salts thereof are contained as an active ingredient.

19 Claims, 9 Drawing Sheets

FOREIGN PATENT DOCUMENTS

| | | |
|---|---|---|
| WO | WO 97/22248 | 6/1997 |
| WO | WO 99/15011 | 4/1999 |
| WO | WO 02/40028 A1 | 5/2002 |

OTHER PUBLICATIONS

Database CAPLUS Chemical Abstracts Service, Columbus, Ohio, US; Database Accession No. 1999:399084, Abstract of Zheng et al., Chemical & Pharmaceutical Bulletin (1999), 47(6), 777-782.*

Database CAPLUS Chemical Abstracts Service, Columbus, Ohio, US; Database Accession No. 1999:3017, Abstract of Zheng et al., Chemical & Pharmaceutical Bulletin (1998), 46(12), 1950-1951.*

Database CAPLUS Chemical Abstracts Service, Columbus, Ohio, US; Database Accession No. 2005:731613, Abstract of JP 2005213159.*

Database CAPLUS Chemical Abstracts Service, Columbus, Ohio, US; Database Accession No. 2005:731613, Abstract of Natori, JP 2005213159.*

Shunji Natori, 'Konchu no Seitai Bogyo Bunshi Kiko to Sono Oyo', Senryakuteki Kiso Kenkyu Suishin Jigyo Kenkyu Nenpo, 2000, pp. 180-184 (partial English translation).

Shunji Natori, "3 Senchi Nikubae no Seitai Bogyo System", Biomedical Perspectives, vol. 7, No. 1, 1998, pp. 77-83 (with English translation).

Pharma Medica, vol. 8, No. 4, 1990, pp. 11-14.

Clinical Neuroscience, vol. 19, No. 5, May 2001, pp. 22:520 to 22:525.

Brett Garner, et al., "Formation of Hydroxyl Radicals in the Human Lens is Related to the Severity of Nuclear Cataract", Exp. Eye Res., 2000, vol. 70, No. 1, pp. 81-88.

Jae Yoon Leem, et al., "Purification and Characterization of N-β-Alanyl-5-S-glutathionyl-3,4-dihydroxyphenylalanine, a Novel Antibacterial Substance of *Sarcophaga peregrina* (Flesh Fly)", The Journal of Biological Chemistry, vol. 271, No. 23, Jun. 7, 1996, pp. 13573-13577.

Nobuko Akiyama, et al., "Involvement of $H_2O_2$ and $O_2-$ in the cytotoxicity of N-β-Alanyl-5-S-glutathionyl-3,4-dihydroxyphenylalanine (5-S-GAD), a novel insect-derived anti-tumor compound", Cancer Sci., vol. 94, No. 4, Apr. 2003, pp. 400-404.

Shosuke Ito, et al., "Synthesis and Antitumor Activity of Cysteinyl-3,4-dihydroxyphenylalanines and Related Compounds", J. Med. Chem., 1981, 24, pp. 673-677.

Shunji Natori, Relation between insect defense proteins and development of flesh fly, *Sarcophaga peregrina*, 1998, pp. 245-260.

Prota, et al., Gazzetta Chimica Italiana (1968), 98(4), 495-510.

Jeremy P. E. Spencer, et al., "Conjugates of Catecholamines with Cysteine and GSH in Parkinson's Disease: Possible Mechanisms of Formation Involving Reactive Oxygen Species", Journal of Neurochemistry 199811 US, vol. 71, No. 5, XP002538225, Nov. 1998, pp. 2112-2122.

Zhe-bin Zheng, et al., "Selective Inhibition of Src Protein Tyrosine Kinase by Analogues of 5-S-Glutathionyl-β-alanyl-L-Dopa", Chemical and Pharmaceutical Bulletin, Pharmaceutical Society of Japan, vol. 46, No. 12, XP002991712, Dec. 1, 1998, pp. 1950-1951.

Toshiaki Miura. "Antioxidant Activity of Adrenergic Agents Derived from Catechol", Biochemical Pharmacology, vol. 55, No. 12, XP002538228, Jun. 15, 1998, pp. 2001-2006.

Nobuko Akiyama, et al. "A Long-Lived o-Semiquinone Radical Anion is Formed From N-β-alanyl-5-S-Glutathionyl-3,4-Dihydroxyphenylalanine (5-S-GAD), an Insect-Derived Antibacterial Substance", Journal of Biochemistry, The Japanese Biochemical Society, vol. 142, No. 1, XP002538229, Jul. 2007, pp. 41-48.

Kaagedal, et al., Analytical Biochemistry (1987), 165(1), 167-74.

Ambani L.M., et al., "Brain Peroxidase and Catalase in Parkinson Disease", Archives of Neurology, American Medical Association, Chicago, IL, US, vol. 32, No. 2, Feb. 1, 1975, pp. 114-118, XP009137521ISSN: 0003-9942.

Office Action as received in the corresponding European Patent Application No. 06 757 009.3 dated Oct. 21, 2010.

Joshua W. Miller, et al., "Oxidative Damage Caused by Free Radicals Produced During Catecholamine Autoxidation: Protective Effects of O-Methylation and Melatonin", Free Radical Biology & Medicine, vol. 21, No. 2, pp. 241-249 (1996).

Christos Polytarchou, et al., "Antioxidants Inhabit Angiogenesis In Vivo through Down-regulation of Nitric Oxide Synthase Expression and Activity", Free Radical Research, vol. 38, No. 5, May 2004, pp. 501-508.

Jung Hoon Kang, "Modification of Cu,Zn-Superoxide Dismutase by Oxidized Catecholamines", Journal of Biochemistry and Molecular Biology, vol. 37, No. 3, May 2004, pp. 325-329.

Office Action issued Sep. 27, 2011, in Japanese Patent Application No. 2007-520104.

Arno G. Siraki, et al., "Superoxide radical scavenging and attenuation of hypoxiareoxygenation injury by neurotransmitter ferric complexes in isolated rat hepatocytes", Neuroscience Letters, vol. 296, 2000, pp. 37-40.

Jakob P. Ley, et al., "Synthesis of Lipophilic Clovamide Derivatives and Their Antioxidative Potential against Lipid Peroxidation", Journal of Agricultural and Food Chemistry, vol. 51, No. 16, 2003, pp. 4596-4602.

* cited by examiner

| GRADE | FRONT VIEW | SLIT VIEW |
|---|---|---|
| 1 | Pre-Equatorial Vacuolation | |
| 2 | Sub-Epithelial Vacuolation (Opaque Plaques and Water Clefts) | Posterior Cortical Reflex |
| 3 | Cloudy Lens with Posterior Cortical Opacification | cloudy lens — Posterior Cortical Opacification |
| 4 | Nuclear Opacification — visible to naked eye | narrow ant. chamber — cloudy lens — Opacification |
| 5 | Completely Opaque Lens | |

*Fig. 12*

RADICAL SCAVENGER AND ACTIVE OXYGEN ELIMINATING AGENT

CROSS-REFERENCE TO RELATED APPLICATIONS

This application is a divisional application of U.S. Ser. No. 11/916,942 filed Dec. 7, 2007 which was a 371 application of PCT/JP06/311269 filed Jun. 6, 2006 and claims the benefit of JP 2005-166842 filed Jun. 7, 2005.

TECHNICAL FIELD

The present invention relates to novel uses of 3,4-dihydroxyphenylalanine derivatives such as N-β-alanyl-5-S-glutathionyl-3,4-dihydroxyphenylalanine (5-S-GAD) or salts thereof (radical scavenger, active oxygen-scavenging agent and the like).

BACKGROUND ART

As biological target molecules to be damaged with free radicals, for example, lipid, sugar, nucleic acid, enzyme, and protein are important. In particular, highly unsaturated fatty acids locally existing in lipids in all cellular membranes are attacked with free radicals, to generate lipid peroxides through lipid peroxidation chain reactions. Direct or indirect actions with these lipid peroxides are considered as one cause of biological membrane damages by free radicals. Biological membrane is composed of lipid and protein, which not only works as a partition wall separating cells and small organs but also forms places with accumulated diverse functions, including for example a source of physiologically active substances or a function as anchors for enzymes and receptors on membrane surfaces. Therefore, lipid peroxidation chain reactions, induced by free radicals, not only give damages to membrane structures but also seriously disrupt enzymatic reactions and receptor functions of proteins, which are working in such membrane structures. When such lipid peroxidation chain reactions occur in any organ or cell, damages naturally occur at that site and sometimes induce a specific disease. Furthermore, it is known that lipid peroxide flows out of local sites into blood circulation, which consequently causes secondary lesions primarily including vascular lesions.

Typical examples thereof are complications of diabetes mellitus, complications of renal impairment, multiple organ impairment during shocks, and the like. Methionine-, histidine-, cystine-, tyrosine- and tryptophan residues are amino acid residues readily oxidizable with free radical and/or active oxygen. Via such oxidative modifications, an enzyme is irreversibly inactivated and simultaneously decomposed readily with protease (such oxidative inactivation of enzymes simultaneously leads to the leukocyte sterilization action).

Meanwhile, nucleic acid damages with free radical and/or active oxygen are very important in view of cancer and aging. It has been demonstrated that free radical and/or active oxygen interacts with and oxidizes any of the bases, sugars and ester bonds of nucleic acids. It is reported that active oxygen generated with xanthine-xanthine oxidase, from leukocyte activated with phorbol ester or from tobacco smoke makes DNA cleavage. As to the role of sugar-derived free radicals in biological organisms, for example, auto-oxidation of glucose, lipid peroxidation and intracellular sugar metabolisms suggest that aldehydes such as glyoxal, methyl glyoxal, glycol aldehyde, 3-deoxyglucoson and glucoson with higher reactivities than those of glucose are deeply involved in the preparation of advanced glycation endproducts (AGE) from proteins. It is considered that the depolymerization of hyauloronic acid with active oxygen is a cause of the reduction of the viscosity of synovial fluid in chronic articular rheumatism. Main diseases specifically involving free radical and/or active oxygen are listed below.

Cataract, damages due to ophthalmologic surgeries, damages with the use of contact lenses, damages due to cornea transplantation, open-angle glaucoma (POAG), corneal diseases, dry eye, bleary eye, macular degeneration, retinal degeneration (age-related macular degeneration), retinopathy of prematurity, eye siderosis, uveal disease, cerebral infarction, cerebral ischemia, cerebral edema, myocardial infarction, ischemic reperfusion disorders, renal reperfusion, arrhythmia, arterial sclerosis, head injuries, cerebral injuries, medulla injuries, rheumatism, inflammation, periodontal disease, odontitis, uveitis, eczema/dermal inflammation, ultraviolet (dermal) damages, autoimmune diseases (rheumatism, etc.), diabetes mellitus, gastritis/gastric ulcer (gastric mucosa damages), liver diseases (drug-induced liver disorders), ulcerative colitis, Crohn's disease (IBD), ischemic colitis, adult respiratory distress syndrome (ARDS), Down syndrome, schizophrenia, epilepsia, neural degeneration diseases, Alzheimer's disease, Parkinson's disease (DIC), aging, amyotropic lateral sclerosis (ALS), hemolytic diseases, disseminated intravascular coagulation (DIC) syndrome, septic shock, traumatic shock, flap necrosis, edema, paraquat poisoning, accelerated vasopermeability, lung emphysema, acute pancreatitis, porphyrrinemia, Mediterranean anemia, and the increase of active oxygen or other free radicals as induced by burn, frostbite, radiation, drugs or hemodialysis (non-patent references 1,2).

Cataract is a disease involving lower vision due to the opacification of ocular lens. Other than the change of the structure via the glycation of ocular lens proteins, the involvement of oxidative stress is remarked as the etiology (non-patent reference 3). Near-ultraviolet ray at 300 to 400 nm, which is absorbed into the lens, generates active oxygen to progress the association of lens proteins and lipid peroxidation, so that polymeric substances and insoluble proteins are generated, which work to enhance scattered light/yellow tone (non-patent reference 3). In eyes with cataract in humans compared with normal lens in humans in the same age group, the reduction of the activities of enzymes such as superoxide dismutase (SOD), glutathione peroxidase (GPx) or catalase, the decrease of ascorbic acid or glutathione of reduced type (GSH), and the increase of lipid peroxides are observed, as noted (non-patent reference 3).

N-β-Alanyl-5-S-glutathionyl-3,4-dihydroxyphenylalanine (5-S-GAD) is a known compound with pharmacological actions for example antibacterial action and anti-cancer action (patent reference 1, non-patent reference 4), an action functioning for inhibiting the formation of osteoclast (patent reference 2), and an anti-cancer action against melanoma or breast cancer (patent reference 3).

[Non-patent reference 1] Pharma Medica, 8(4), 11-14 (1990).
[Non-patent reference 2] Clinical Neuroscience, 19(5), 520-525 (2001).
[Non-patent reference 3] Exp Eye Res. 2000, 70(1):81-8
[Non-patent reference 4] J. Biol. Chem. 1996, 271:13573-13577.
[Non-patent reference 5] Cancer Sci. 2003, 94(4): 400-4.
[Patent reference 1] Official Gazette of Japanese Patent No. 3634894
[Patent reference 2] Official Gazette of Japanese Patent No. 3586809
[Patent reference 3] JP-A-2001-213799

DISCLOSURE OF THE INVENTION

Problems that the Invention is to Solve

Synthetic, low-molecular compounds with strong actions such as dibutyl hydroxy toluene (BHT), butyl hydroxyanisole (BHA) and EDTA-2Na among conventionally known radical scavengers are problematic in terms of safety profile, absorption, metabolism and the like, while natural compounds with great safety profiles, absorption, metabolism and the like such as vitamin E derivatives, ascorbic acid, quercetin and various polyphenols have weak actions, disadvantageously.

Thus, it is an object of the invention to provide a radical scavenger, an active oxygen-scavenging agent, an antioxidant agent, an agent for preventing and therapeutically treating diseases or symptoms due to free radical or active oxygen, an ophthalmologic pharmaceutical composition, and a composition for organ storage or organ perfusion, all of which are novel.

Means for Solving the Problems

So as to solve the problems, in accordance with the invention, there are provided a radical scavenger, an active oxygen-scavenging agent, an antioxidant agent, an agent for preventing and therapeutically treating diseases or symptoms due to free radicals or active oxygen, an ophthalmologic pharmaceutical composition, and a composition for organ storage or organ perfusion, where those described above contain a 3,4-dihydroxyphenylalanine derivative represented by the following formula (I):

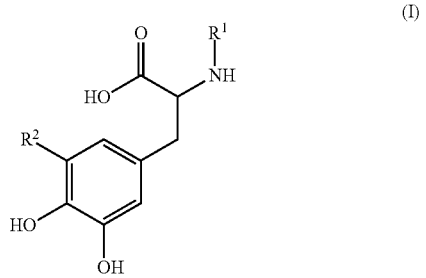

[in the formula, $R^1$ represents hydrogen atom or an appropriate amino acid residue; $R^2$ represents hydrogen atom or a group represented by the following formula (II):

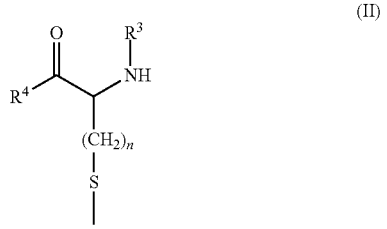

[in the formula, $R^3$ represents hydrogen atom or an appropriate amino acid residue; $R^4$ represents hydroxyl group or an appropriate amino acid residue; and n represents 1 or 2]; when either one of $R^1$ and $R^2$ is hydrogen atom, herein, the remaining one is never hydrogen atom],
or a pharmaceutically acceptable salt thereof as an active ingredient.

In accordance with the invention, the 3,4-dihydroxyphenylalanine derivative is preferably N-β-alanyl-5-S-glutathionyl-3,4-dihydroxyphenylalanine.

Advantages of the Invention

In accordance with the invention, there are provided a radical scavenger, an active oxygen-scavenging agent, an antioxidant agent, an agent for preventing and therapeutically treating diseases or symptoms due to free radicals or active oxygen, an ophthalmologic pharmaceutical composition, and a composition for organ storage or organ perfusion, all of which are novel.

BRIEF DESCRIPTION OF THE DRAWINGS

FIG. 12 Severity of cataract according to the Cotlier standard.

BEST MODE FOR CARRYING OUT THE INVENTION

Figure 1:
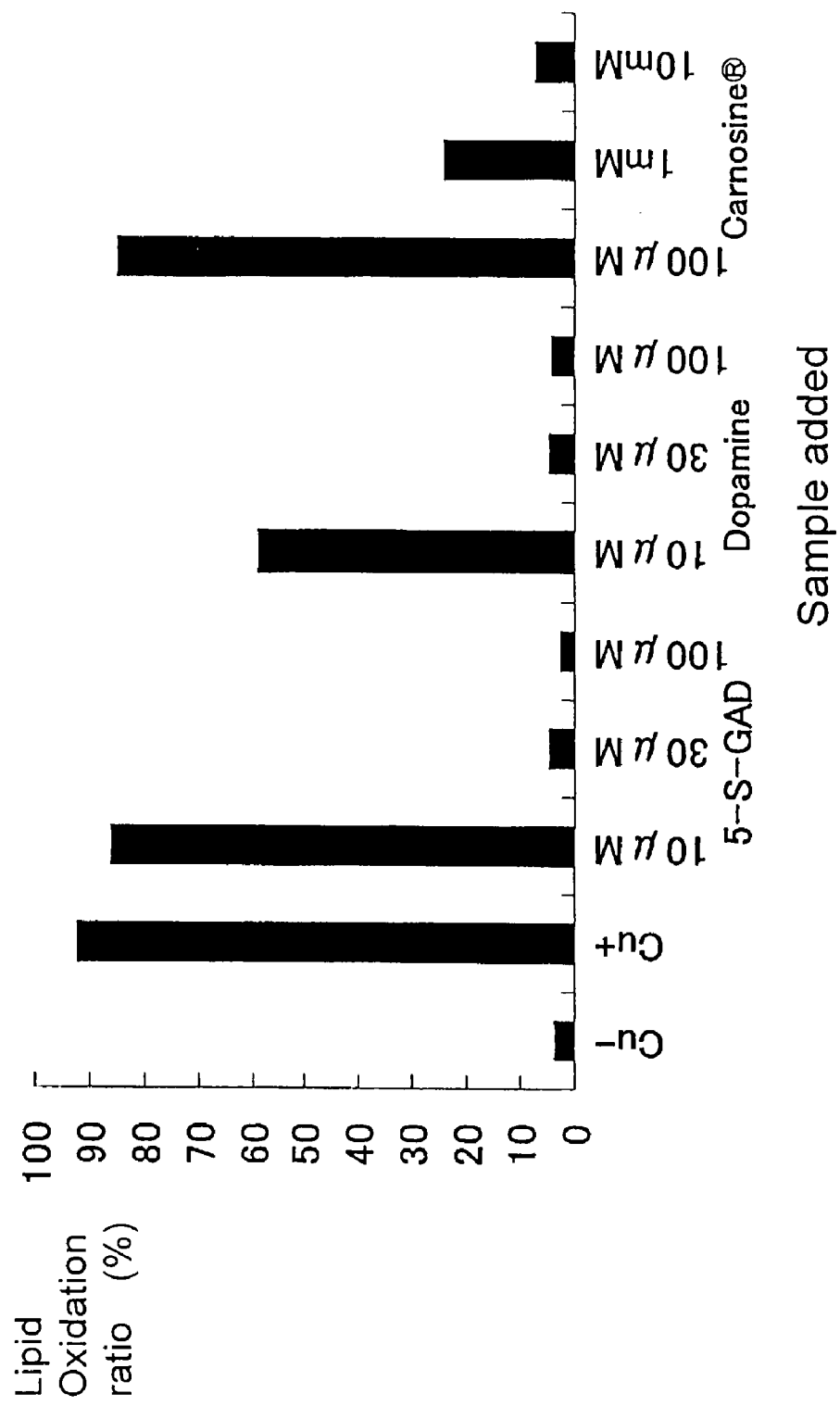
FIG. 1 A view depicting the comparison in the action of suppressing lipid peroxides between N-β-alanyl-5-S-glutathionyl-3,4-dihydroxyphenylalanine (5-S-GAD) and control compounds.

An appropriate amino acid residue represented by $R^1$, $R^3$ or $R^4$ includes any amino acid residue of any type, for example α-amino acid residues, β-amino acid residues, γ-amino acid residues, residues of neutral amino acids (monoamino monocarboxylic acids such as glycine, valine, and leucine), residues of acidic amino acids (monoamino dicarboxylic acids such as glutamic acid, and aspartic acid), and residues of basic amino acids (diamino monocarboxylic acids such as arginine and phenylalanine). Herein, the bonding mode of an appropriate amino acid residue represented by $R^1$, $R^3$ or $R^4$ is via the amide bond.

The amino acid residue represented by $R^1$ is preferably the β-alanine residue; the amino acid residue represented by $R^3$ is preferably the glutamic acid residue; the amino acid residue represented by $R^4$ is preferably the glycine residue; and n is preferably 1.

3,4-Dihydroxyphenylalanine derivative represented by the formula (I) (compound (I)) is preferably N-β-alanyl-5-S-glutathionyl-3,4-dihydroxyphenylalanine (5-S-GAD), β-alanyl-3,4-dihydroxyphenylalanine (β-AD), or 5-S-cysteinyl-3,4-dihydroxyphenylalanine (5-S-CD). When the compound (I) is 5-S-GAD, $R^1$ is the β-alanine residue; $R^2$ is a group represented by the formula (II); $R^3$ is the glutamine residue; $R^4$ is the glycine residue; and n is 1. When the compound (I) is β-AD, $R^1$ is the β-alanine residue; $R^2$ is hydrogen atom. When the compound (I) is 5-S-CD, $R^1$ is hydrogen atom; $R^2$ is a group represented by the formula (II); $R^3$ is hydrogen atom; $R^4$ is the hydroxyl group; and n is 1.

Asymmetric carbons exist in the compound (I). Those asymmetric carbons exist in any configurations with no specific limitation. The configuration may be S-form or R-form. When the compound (I) exists in the forms of isomers based on one or two or more asymmetric carbons, the compound (I) may be an appropriate isomer in a stereochemically pure form (optical isomer, diastereomer, etc.) or may be a mixture or racemate of appropriate isomers. For example, 5-S-GAD has asymmetric carbons at three positions within the molecule, so 5-S-GAD has isomers of various optically active compounds, partially optically active compounds, and racemates. 5-S-GAD may exist in the form of any one of them or may exist in the form of a mixture of two or more thereof. Preferably, 5-S-GAD is an optically active compound represented by the following formula.

5-S-GAD

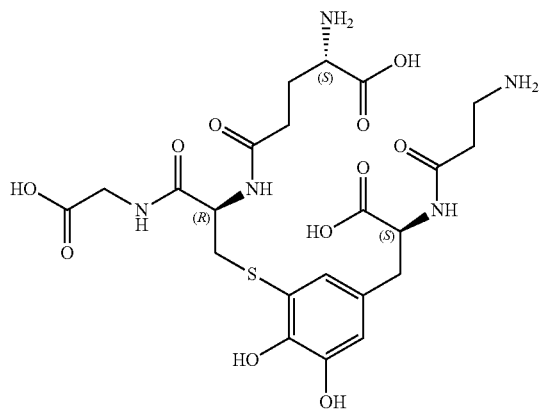

Pharmaceutically acceptable salts of the compound (I) include for example acid addition salts, base addition salts, and amino acid addition salts. The acid addition salts include for example inorganic acid salts such as hydrochloride salts, hydrobromate salts, sulfate salts, and phosphate salts and organic acid salts such as formate salts, acetate salts, oxalate salts, benzoate salts, methane sulfonate salts, p-toluene sulfonate salts, maleate salts, fumarate salts, tartrate salts, citrate salts, succinate salts, and lactate salts. The base addition salts include for example metal salts such as sodium salts, potassium salts, magnesium salts, and calcium salts; ammonium salts; and amine salts such as methylamine salts, and triethylamine salts. The amino acid addition salts include for example salts with added glycine, phenylalanine, aspartic acid and glutamic acid.

The compound (I) typically including 5-S-GAD, β-AD and 5-S-CD can be produced according to known methods for producing them, as disclosed in JP-A-Hei 8-337594; JP-A-2001-213799; JP-A-2001-226283; J Biol Chem, 271, 13573-13577 (1996) by Leem J Y, et al.; J Med Chem, 124, 673-677 (1981) by Ito S, et al.; Molecular Mechanisms of Immune Reponses in Insects by Natori S., London, Chapman & Hall, 245-260 (1998); and the like.

A specific method for producing the compound (I) is as follows.

The amino group of an appropriate amino acid is protected with t-butoxycarbonyl group (Boc group), and concurrently, the carboxyl group of the amino acid is modified into an active ester, using N-hydroxysuccinimide (NHS), for reaction with Dopa. In such manner, the compound (I) with an appropriate amino acid as $R_1$ and hydrogen atom as $R_2$ can be produced. So as to purify the compound (I) from the resulting reaction mixture, for example, 1N hydrochloric acid is added to the reaction mixture for an extraction treatment with ethyl acetate under acidic conditions. Subsequently, the ethyl acetate layer is concentrated under reduced pressure, to recover the deposited crystal, which is then treated by HPLC.

The compound (I) with an appropriate amino acid as $R_1$ and a group represented by the formula (II) as $R_2$ can be produced by dissolving the compound (I) with an appropriate amino acid as $R_1$ and hydrogen atom as $R_2$, together with the compound (III) represented by the following formula (III):

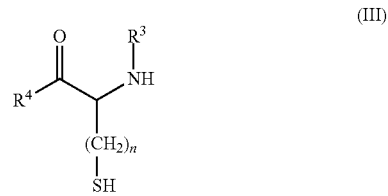

(III)

[in the formula, $R^3$, $R^4$ and n have the same meanings as described above], in a phosphate buffer, for tyrosinase treatment. The compound (I) can be purified from the reaction solution by HPLC treatment.

Furthermore, the compound (I) with hydrogen atom as $R^1$ and a group represented by the formula (II) as $R^2$ can be produced by dissolving Dopa together with the compound (III) in a phosphate buffer, for tyrosinase treatment. The compound (I) can be purified from the reaction solution by HPLC treatment.

The compound (III) can be produced by bonding an appropriate amino acid to the amino group of a compound (IV) represented by the following formula (IV) (for example, cysteine, homocysteine):

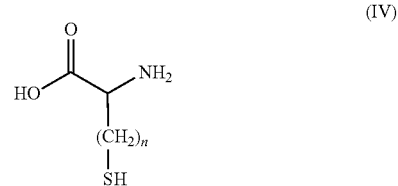

(IV)

[in the formula, n has the same meaning as described above] and to the carboxyl group thereof, via amide bonding.

5-S-GAD may be obtained by extraction from naturally occurring substances by the method described in the official gazette of the Japanese Patent No. 3634894 or may be synthetically prepared chemically according to for example the method described in J. Biol. Chem. 1996, 271:13573-13577. For example, 5-S-GAD can be obtained by scratching an adult fly of Sarcophaga peregrina and then feeding the adult fly, to collect the body fluid or to homogenate the adult fly, which is then used as a raw material for separation and fractionation by ion column chromatography and reverse-phase HPLC, to collect a fraction with an antibacterial activity.

The compound (I) has a free radical (free group)-capturing action, an active oxygen-scavenging action and the like. A free radical (free group) to be captured by the compound (I) includes for example but is not limited to superoxide, hydroxyl radical, and DPPH. An active oxygen species to be scavenged by the compound (I) includes for example but is not limited to superoxide, hydrogen peroxide, hydroxyl radical, and singlet oxygen. Because the compound (I) has a free radical (free group)-capturing action or an active oxygen-scavenging action, the compound (I) can be used as a radical scavenger or an active oxygen-scavenging agent. Additionally because the compound (I) is capable of exerting effects on the prevention of substance oxidation with free radical or active oxygen, the prevention or therapeutic treatment of diseases or symptoms due to free radical or active oxygen, the prevention of damages (for example, damages of endothelial cells) of organs (for example, organs for transplantation) with free radical or active oxygen, and the like through the free radical (free group)-capturing action or the active oxygen-scavenging action, the compound can be used as an antioxidant agent, a prophylactic agent and a therapeutic agent of diseases or symptoms due to free radical or active oxygen, a composition for organ storage or organ perfusion and the like.

Diseases or symptoms due to free radical or active oxygen, which can be prevented or therapeutically treated via the free radical (free group)-capturing action or the active oxygen-scavenging action, include for example cataract; damages following ophthalmologic surgeries; damages with the use of contact lenses; damages following cornea transplantation; open-angle glaucoma (POAG); corneal diseases; dry eye; bleary eye; macular degeneration; retinal degeneration (age-related macular degeneration); retinopathy of prematurity; eye siderosis; uveal disease; cerebral infarction; cerebral ischemia; cerebral edema; myocardial infarction; ischemic reperfusion disorders; renal reperfusion; arrhythmia; arterial sclerosis; head injuries; cerebral injuries; medulla injuries; rheumatism; inflammation; periodontal disease; odontitis; uveitis; eczema/dermal inflammation; ultraviolet (dermal) damages; autoimmune diseases (rheumatism, etc.); diabetes mellitus; gastritis/gastric ulcer (gastric mucosa damages); liver diseases (drug-induced liver disorders); ulcerative colitis; Crohn's disease (IBD); ischemic colitis; adult respiratory distress syndrome (ARDS); Down syndrome; schizophrenia; epilepsia; neural degeneration diseases; Alzheimer's disease; Parkinson's disease (DIC); aging; amyotropic lateral sclerosis (ALS); hemolytic diseases; disseminated intravascular coagulation (DIC) syndrome; septic shock; traumatic shock; flap necrosis; edema; paraquat poisoning; accelerated vasopermeability; lung emphysema; acute pancreatitis; porphyrrinemia; Mediterranean anemia; and the increase of active oxygen or other free radicals induced by burn, frostbite, radiation, drugs or hemodialysis.

For preparing such composition for various uses, the compound (I) may be used singly to prepare the intended composition. Generally, however, a pharmaceutically acceptable one or more carriers and/or additives are used together with the compound (I), to prepare the intended composition. In that case, the amount of the compound (I) to be blended may appropriately be adjusted.

The pharmaceutically acceptable carriers include for example, water, pharmaceutically acceptable organic solvents, collagen, polyvinyl alcohol, polyvinylpyrrolidone, carboxyvinyl polymer, sodium alginate, water-soluble dextran, sodium carboxymethyl starch, pectin, gum xanthan, gum Arabic, casein, gelatin, agar, glycerin, propylene glycol, polyethylene glycol, vaseline, paraffin, stearyl alcohol, stearic acid, human serum albumin, mannitol, sorbitol, and lactose.

The additives for general use in such preparation include for example excipients, binders, lubricants, dispersants, suspending agents, emulsifiers, buffers, antioxidants, preservatives, isotonic agents, pH-adjusters, dissolution agents, and stabilizers. These additives may appropriately be selected, depending on the unit dosage form and the like.

Most effective administration route and dosage form are preferably used for the treatment. A general example of the administration route includes oral administration, and parenteral administrations such as intra-cerebral administration, intraperitoneal administration, intra-oral cavity administration, administration into air way, intra-rectum administration, subcutaneous administration, intramuscular administration and intravenous administration. One general example of the dosage form includes tablets, granules, fine granules, capsules, powders, liquids, suspensions, syrups, spraying agents, liposome agents, emulsions, suppositories, injections, eye drops, ointments and tapes.

The ophthalmologic pharmaceutical composition can be prepared into dosage forms for example eye drops, eye rinsing agents, eye ointments, and implants (into sclerotic coat), using a pH adjuster, an isotonic agent, a chelating agent, a thickener, a surfactant, a water-soluble polymer, a polyhydric alcohol, inorganic salts, sugars, an amino acid, vitamin, preservatives/anti-fungal substances, an antioxidant, and an ultraviolet absorber. The amount of the compound (I) to be blended may be adjusted, depending on the dosage form. When N-β-alanyl-5-S-glutathionyl-3,4-dihydroxyphenylalanine (5-S-GAD) is to be blended, for example, the amount thereof to be blended is generally within a range of 0.0005 to 2.0% by mass, preferably a range of 0.001 to 0.5% by mass for eye drops, preferably a range of 0.001 to 0.2% by mass for eye rinsing agents, preferably a range of 0.01 to 1.0% by mass for eye ointments, and preferably a range of 0.01 to 5.0% by mass for injections for use in the administration into vitreous body. The compound (I) may be stored in a container, to which a dissolution solution is added on use to prepare an ophthalmologic pharmaceutical composition, such as eye drops. The ophthalmologic pharmaceutical composition after preparation is preferably stored in a refrigerator under a dark condition. The ophthalmologic pharmaceutical composition is preferably adjusted to physico-chemical conditions (pH, osmotic pressure, etc.) within biologically acceptable ranges. The pH is generally 4.0 to 9.0, preferably 4.3 to 8.5, more preferably 4.5 to 8.0. The osmotic pressure is generally 100 to 1,200 mOsm, preferably 100 to 600 mOsm, more preferably 150 to 400 mOsm. The osmotic pressure against physiological saline is generally 0.3 to 4.1, preferably 0.4 to 2.1, particularly preferably 0.5 to 1.6. The pH, the osmotic pressure and the like may be adjusted, using pH adjusters, isotonic agents, salts and the like, according to general methods.

When the ophthalmologic pharmaceutical composition is to be administered into an eye including cornea, an injection containing the compound (I) as the active ingredient is first prepared, which is then directly injected into a lesion tissue such as cornea and vitreous body or adjacent tissues, using an injection needle. Using a pump or the like, the injections may be administered as an intraocular perfusion solution. By preliminarily immersing a contact lens in the compound (I) as an ingredient in the contact lens, the compound (I) can be administered into an eye including cornea.

Sclerotic coat is a non-vascular, thin layer comprising highly regulated collagen net-work tissues enclosing most of eye peripheries in vertebrate animals. Because sclerotic coat is non-vascular, essentially no risk of bleeding occurs even when injections are done into sclerotic coat. Additionally, injected substances are never immediately lost from eyes. Therefore, sclerotic coat can be utilized as a naturally occurring place for storing drugs. By utilizing sclerotic coat as a naturally occurring place for storing drugs, additionally, the drugs may be supplied to a tissue in a lower layer.

Additionally, the compound (I) can be incorporated into a pellet or a micro-capsule of a sustained release type polymer, to prepare a sustained-release agent, which can be transplanted into a tissue to be therapeutically treated, in a surgical manner. Sustained-release polymers include for example ethylene vinyl acetate, polyhydroxymethacrylate, polyacrylamide, polyvinylpyrrolidone, methylcellulose, lactate polymer, lactic acid/glycolic acid copolymer. Among them, for example, bio-degradable polymers, namely lactate polymer and lactic acid/glycolic acid copolymer, are preferable. A case to be referenced for using sustained-release agents is the use of inserting agents and implanting agents (U.S. Pat. No. 4,863,457). These release drugs over a long period of time onto eyes or into eyes. Inserting agents are devices inserted onto eyes such as on conjunctiva layer, which generally comprise a polymer matrix containing an active compound. When a sustained-release agent is transplanted into sclerotic coat, the compound (I) released from the sustained-release agent passes through sclerotic coat to be dispersed in eyes.

When the ophthalmologic pharmaceutical composition is to be given, the number of doses per day is not limited. Generally, however, the composition can be given once to ten times per day into a single eye or both the eyes, depending on the states of symptoms/onset sites, age and the like. For an eye drop, the dose is about 0.2 mL for both the eyes per one eye dropping. For an eye rinsing agent, the dose is about 10 mL for both the eyes. For eye ointments, the dose is about 0.1 g for both the eyes. For an injection, the dose is about 0.1 mL. In case of an eye drop, for example, one to two drops per one dosing at three to five times daily can bring about the desired effects.

The pharmaceutical composition for oral administration can be prepared into dosage forms such as powders, fine granules, granules, tablets, coated tablets and capsules, using excipients, antioxidants, binders, disintegrators, lubricants, colorants and flavoring agents. The excipients include for example lactose, corn starch, purified sugar, glucose, mannitol, sorbit, crystalline cellulose, and silicon dioxide; the binders include for example polyvinyl alcohol, polyvinyl ether, methylcellulose, ethyl cellulose, gum Arabic, tragancanth, gelatin, shellac, hydroxypropylmethylcellulose, hydroxypropylcellulose, polyvinylpyrrolidone, polypropylene glycol/polyoxyethylene/block polymer and meglumine; the disintegrators include for example starch, agar, gelatin powder, crystalline cellulose, calcium carbonate, sodium hydrogen carbonate, calcium citrate, dextrin, pectin, and carboxymethylcellulose/calcium. The lubricants include for example magnesium stearate, talc, polyethylene glycol, silica and hardened vegetable oil. The colorants include for example those accepted as additives in pharmaceutical products. The flavoring agents include for example cocoa powder, mint essence, aromatic powder, mint oil, Borneo camphor, and cinnamon powder. The resulting tablets, the resulting granules and the like may appropriately be coated with sugar coating and the like.

The composition for injections can be prepared, using for example pH adjusters, dissolution agents, isotonic agents, auxiliary dissolution agents, stabilizers and antioxidants.

The external agent can be prepared, using various bases for general use in pharmaceutical products, quasi-pharmaceutical products, cosmetic products and the like, which are for example animal oils and vegetable oils, mineral oils, ester oil, waxes, higher alcohols, fatty acids, silicone oil, surfactant, phospholipids, alcohols, polyhydric alcohols, water-soluble polymers, clay and minerals, purified water, pH adjusters, antioxidants, chelating agents, preservatives/anti-fungal agents, colors and flavors. If necessary, the external agent may be blended with ingredients such as blood circulation-promoting agents, sterilizers, anti-inflammatory agents, cell-activating agents, vitamins, amino acids, moisturizers, and corneum-solubilizing agents.

When the pharmaceutical composition is to be administrated orally, intravenously, intramuscularly, transrectally or transdermally, the dose thereof should be elevated or lowered, depending on the condition such as the age, sex, body weight, and symptom of a patient and the administration route. Generally, the dose is within a range of 0.1 to 1000 mg/kg, preferably 10 to 500 mg/kg, particularly preferably 50 to 100 mg/kg per day per adult. The pharmaceutical agent at the dose may be given every day, or may be given at an interval of several days. For example, the pharmaceutical agent may be given every one day to 4 days.

The composition for organ storage or perfusion, which contains the compound (I) as the active ingredient, may be prepared into dosage forms such as liquids according to general methods. The amount of the compound (I) to be blended is not specifically limited. Generally, however, the amount thereof is 0.01 to 0.2% by mass, preferably 0.02 to 0.1% by mass. When the composition is for the storage or perfusion of a transplanting organ, the composition (I) or a pharmaceutically acceptable salt thereof is added to a known composition for organ storage and with the same composition as that of the intracellular solution at a high potassium content, for example the UW (University of Wisconsin) solution, the ET-Kyoto solution, the Collins solution, the Euro-Collins solution, and the Sachs solution, to prepare the composition for organ storage or perfusion. The physico-chemical properties of the composition for organ storage or perfusion are the same as the composition for organ storage as the base. The pH is generally about 6 to 9, preferably about 7.4, while the potassium concentration is generally about 1 to 10 mM, preferably about 2 to 8 mM, more preferably about 4 to 6 mM.

EXAMPLES

Example 1

Lipid Peroxide-Suppressing Action

As an action of capturing free group (free radical-scavenging action), the effect of N-β-alanyl-5-S-glutathionyl-3,4-dihydroxyphenylalanine (5-S-GAD) on LDL oxidation was examined. As controls, dopamine and Carnosine (under trade name; N-acetylcarnosine as the ingredient name) used as eye drops for cataract were used. LDL was prepared by a fractionation and centrifugation method. A fraction at a specific gravity of 1.019 to 1.063 g/mL in serum was defined as human LDL. 5 µM $CuSO_4$, 5-S-GAD (3 to 100 µM) and N-acetyl-carnosine (100 µM to 10 mM) or L-carnosine (10

μM to 10 mM) were added to 0.2 mg/mL LDL, for incubation at 37° C. for 3 hours. After termination of the incubation, TBARS (a substance reactive with thiobarbituric acid) was assayed. Although the TBA reaction is a non-specific reaction, the reaction is used for a method of assaying various lipid peroxide products including malone dialdehyde. An experiment of peroxidation with copper sulfate was done twice (N=2). An aqueous solution containing 3.75 mg/mL thiobarbituric acid (TBA), 150 mg/mL trichloroacetic acid (TCA) and 0.25 N hydrochloric acid (HCl) was prepared as the TBA reagent, while tetramethoxypropane was used to prepare standard solutions (2, 5, 10, 20, 40 μM). 100 μL each of an LDL sample or a standard solution was added together with 200 μL of the TBA reagent into an Eppendorf tube (1.5 mL), which was then sealed with a cap for thorough mixing. After heating at 95° C. for 15 minutes, the resulting mixture was cooled in water and centrifuged at 3000 rpm for 5 minutes. The supernatant was assayed of the absorbance (535 nm). Based on the absorbance of the standard solutions, a standard curve was prepared. Based on the standard curve, the amount of TBARS in the LDL sample was calculated (in nmol/mg LDL protein) (mean, n=2, see Table 1 and FIG. 1).

TABLE 1

| Samples added | Amount of TBARS (nmol/mg LDL protein) |
|---|---|
| −CuSO₄ | 3.387 |
| +CuSO₄ | 92.165 |
| 10 μM 5-S-GAD | 85.683 |
| 30 μM 5-S-GAD | 4.290 |
| 100 μM 5-S-GAD | 2.649 |
| 10 μM dopamine | 58.853 |
| 30 μM dopamine | 4.454 |
| 100 μM dopamine | 4.208 |
| 100 μM Carnosine | 84.781 |
| 1 mM Carnosine | 23.900 |
| 10 mM Carnosine | 7.079 |

As shown in Table 1 and FIG. 1, N-β-alanyl-5-S-glutathionyl-3,4-dihydroxyphenylalanine (5-S-GAD) exerted an antioxidation action at the same level as that of dopamine and at a 10-fold higher level than that of Carnosine (under trade name).

Example 2

DPPH-Scavenging Action

DPPH (1,1-diphenyl-2-picrylhydrazyl) is one of nitrogen radicals and is a very stable radical, which is commercially available as a black-purple crystal (Wako Pure Chemical, Co., Ltd., etc.). N-β-Alanyl-5-S-glutathionyl-3,4-dihydroxyphenylalanine (5-S-GAD) (see Table 2) or Carnosine (under trade name) (see Table 3) was added to an ethanol solution of 50 mM DPPH radical, for reaction at ambient temperature for 5 minutes (see the following reaction scheme). Instead of the test reagent, distilled water was added to the ethanol solution, which was used as a background. The DPPH absorbance at 517 nm was assayed, to calculate the scavenging ratio (%) of the DPPH radical according to the following equation. The scavenging ratio was defined as radical scavenger activity (mean, n=2; see Table 2, Table 3 and FIG. 2).

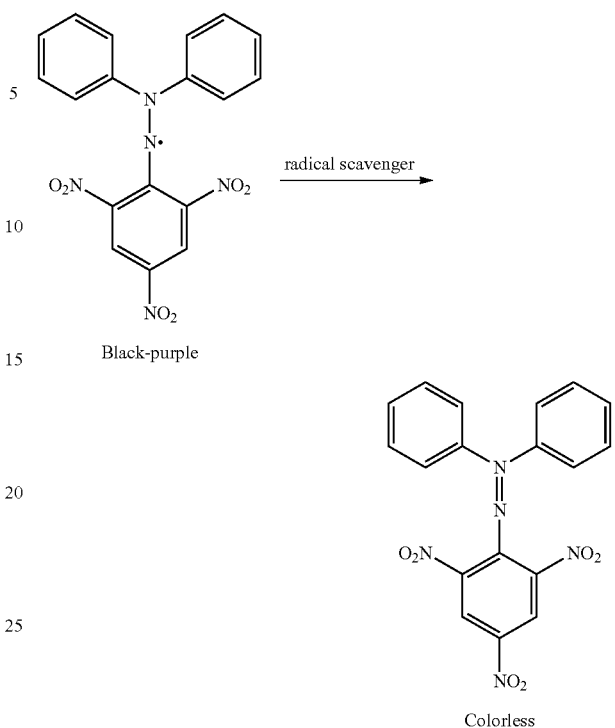

Black-purple radical scavenger →

Colorless

Radical-scavenging ratio (%)=[assay value of background (mean)−assay value of solution at each concentration]/background assay value (mean)]× 100

TABLE 2

| 1) 5-S-GAD | |
|---|---|
| Concentration added (μM) | Radical-scavenging ratio (%) |
| 0 | 0 |
| 1 | 3.918 |
| 3 | 13.891 |
| 10 | 73.762 |
| 30 | 93.487 |

TABLE 3

| 2) Carnosine ® | |
|---|---|
| Concentration added (μM) | Radical-scavenging ratio (%) |
| 0 | 0 |
| 1 | 0.058 |
| 3 | 0.901 |
| 10 | 0.189 |
| 30 | 0.407 |
| 100 | 2.382 |
| 1000 | 4.707 |

Figure 2:
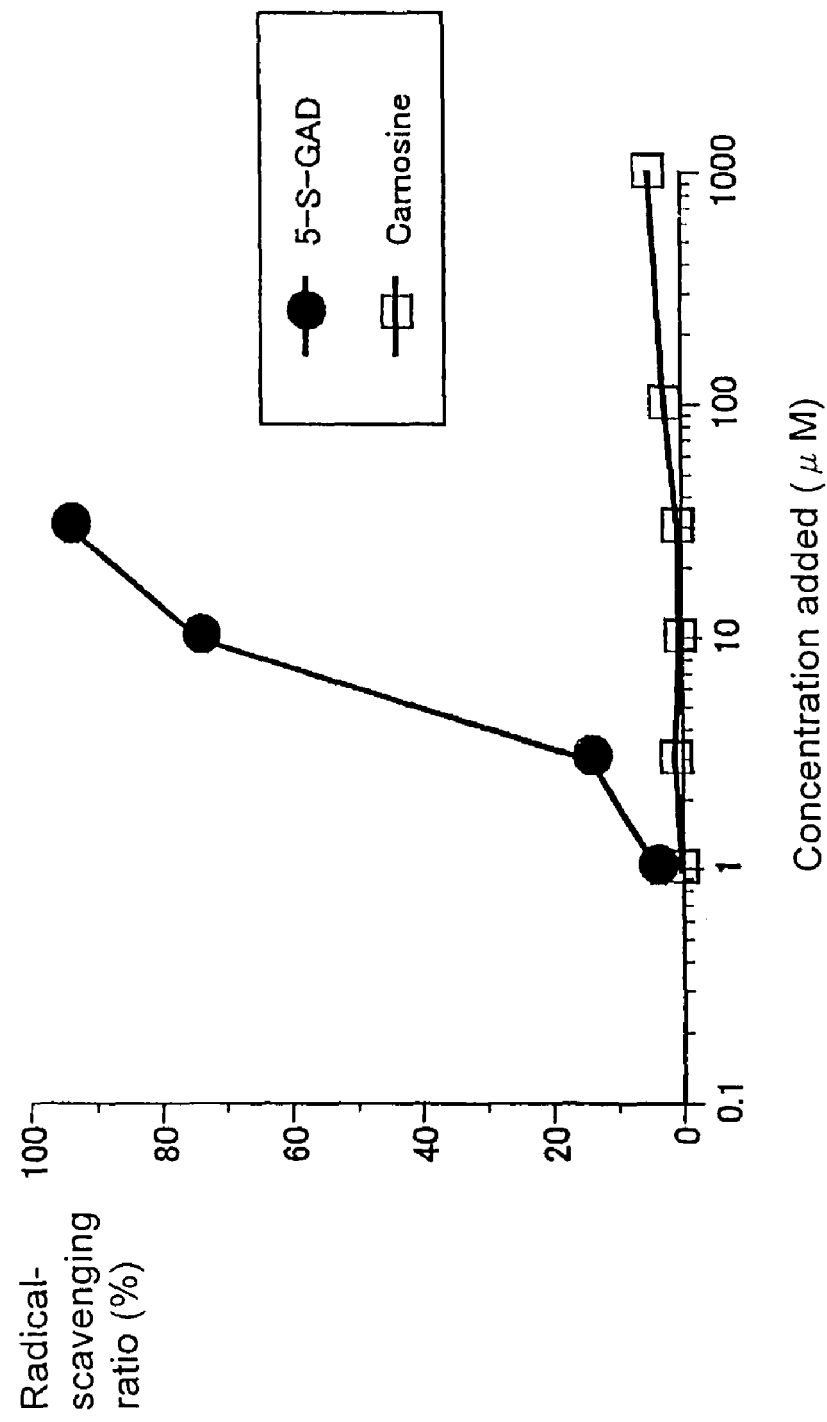
FIG. 2 A view depicting the comparison in the DPPH radical-scavenging activity between N-β-alanyl-5-S-glutathionyl-3,4-dihydroxyphenylalanine (5-S-GAD) and a control compound.

As shown in Table 2, Table 3 and FIG. 2, N-β-alanyl-5-S-glutathionyl-3,4-dihydroxyphenylalanine (5-S-GAD) showed strong actions for scavenging the DPPH radical, while Carnosine (under trade name) was absolutely never effective, as observed.

Example 3

Superoxide Anion ($O^{2-}$)-Scavenging Activity

In a 50 mM carbonate buffer (pH 10) containing 200 μM lucigenin, 100 μM xanthine and 1 mU/mL xanthine oxidase reacted together. The chemiluminescence level depending on the generated superoxide anion ($O^{2-}$) was assayed with BIOLUMAT (under trade name) (Model type LB 9505, manufactured by EG&G BERTHORD Company) for 10 minutes. The area under the curve indicating the total chemiluminescence over the 10 minutes was calculated. Defining the area under the curve for a group (control) added with PBS(−) instead of the test substance solution at the same amount as that of the solution as 100, the effect of N-β-alanyl-5-S-glutathionyl-3,4-dihydroxyphenylalanine (5-S-GAD) (Table 4) or Carnosine (under trade name) (Table 5) on the increase of chemiluminescence was examined. The suppressive activity thereof was defined as superoxide anion-scavenging activity (%) (mean, n=2; see Table 4, Table 5 and FIG. 3).

TABLE 4

| 1) 5-S-GAD | |
|---|---|
| Concentration added (μM) | Radical-scavenging ratio (%) |
| 0.1 | −0.75 |
| 1 | 26.03 |
| 10 | 78.28 |
| 100 | 91.19 |

TABLE 5

| 2) Carnosine ® | |
|---|---|
| Concentration added (μM) | Radical-scavenging ratio (%) |
| 0.1 | −8.45 |
| 1 | −7.98 |
| 10 | −0.28 |
| 100 | −8.79 |
| 1000 | 14.81 |
| 10000 | 9.29 |

Figure 3:
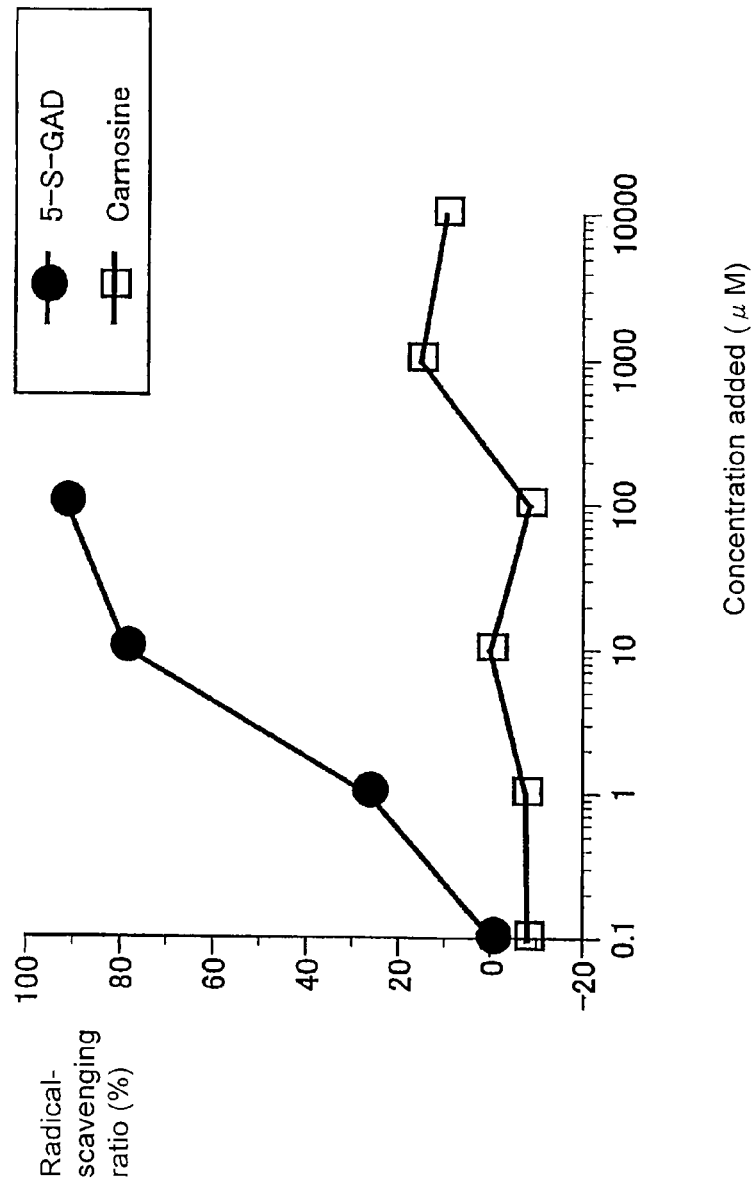
FIG. 3 A view depicting the comparison in the $O^{2-}$-scavenging activity between N-β-alanyl-5-S-glutathionyl-3,4-dihydroxyphenylalanine (5-S-GAD) and a control compound.

As shown in Table 4, Table 5 and FIG. 3, N-β-alanyl-5-S-glutathionyl-3,4-dihydroxyphenylalanine (5-S-GAD) showed strong actions for scavenging the superoxide anion ($O^{2-}$), while Carnosine (under trade name) was absolutely never effective, as observed.

Example 4

Galactosemic Cataract Model

Preparation of Eye Drop 352 mg of a test substance was weighed and then dissolved in 1.1 mL of 1N NaOH (1 mol/L sodium hydroxide; manufactured by Wako Pure Chemical, Co., Ltd.). After dissolution, it was verified with a pH paper (Duotest under trade name; MACHEREY-NAGEL) that the pH was within an acceptable range (5 to 8). Subsequently, the resulting solution was divided in each volume of 0.03 mL into 30 2-ml tubes (28 such tubes for four tests per day for 7 days+2 such tubes for spare). These were immediately frozen in liquid nitrogen, and stored under freezing (preset at −85° C. within an acceptable range of −90 to −75° C.)/dark conditions. The solutions under storage were defined as stock solution at 320 mg/mL. The stock solutions could be used within 8 days after the preparation. The stock solutions outside the 8-day period after the preparation were disposed.

Before eye dropping, the following preparation was done. After the tubes of the stock solution at 320 mg/mL were back to ambient temperature, 0.93 mL of physiological saline was directly added to the tubes for dilution. After preparative dilution, it was verified with a pH paper that the pH of the diluted solutions were within an acceptable range (5 to 8). The resulting eye drop was defined as 1.0% eye drop for use in administration. 0.09 mL of the 1.0% eye drop was divided in a 2-mL tube, to which 0.81 mL of physiological saline was directly added for dilution. Subsequently, it was verified with a pH paper that the pH of the diluted solution was within an acceptable range (5 to 8). The resulting eye drop was defined as 0.1% eye drop, for use in administration. Herein, eye drops of pH outside the acceptable range were never used. The 1.0% eye drop and the 0.1% eye drop practically used for administration were at pH 5.2 to 8.0 and pH 6.2 to 7.4, respectively. As the medium, physiological saline as the control substance was used as it was.

Preparation of Cataract Model

Male Crj:CD(SD) IGS rats (SPF) of age 3 weeks were subjected to a 5-day quarantine period and then to an 8-day acclimatization period. By the random extraction method, the rats were grouped in 3 groups, where each group consisted of 10 rats, in a manner such that the average body weight and deviation in each group might be almost equal. After grouping, the rats were fed ad libitum with a powdery feed containing galactose at 50% [a powder feed (Lot No. 050107) of a mixture at equal amounts of CRF-1 powder feed (Lot No. 041104; manufacturer: Oriental Yeast Co., Ltd.) and galactose (D-galactose, Lot No. QYG0223, manufacturer: Yoneyama Pharmaceutical Industry, Co. Ltd.); the mixture was prepared by Oriental Yeast Co., Ltd.; abbreviated as {galactose feed}] hereinafter], as placed in a powder feeder. Additionally, the rats were fed ad libitum with drinking water.

Administration Method

The three groups were defined as (A) medium control group, (B) 0.1% 5-S-GAD eye drop group, and (C) 1.0% 5-S-GAD eye drop group for dosing. The administration route was eye dropping as a clinically prospective route. The number of eye dropping per day was four times, while the interval between eye droppings was about 2 hours. The eye dropping was done around 9:30 am (9:00 am to 10:00 am as the defined time period), around 11:30 (11:00 am to 12:00 am as the defined time period), around 13:30 (13:00 pm to 14:00 pm as the defined time period) and around 15:30 pm (15:00 pm to 16:00 pm as the defined time period). Eye dropping was done over 28 days.

On day 1, day 7, day 14, day 21 and day 28, ophthalmologic examinations were done about 30 minutes after each last eye dropping. The observation method is as follows. Right eye with eye drop application and left eye without any treatment were observed of their lenses, using a slit lamp (SL-15, Kowa Company, Ltd.). The severity of cataract was evaluated, according to the Cotlier standard (see FIG. 1 in Arch Ophthalmol., (67) 476-82, 1962, which was entitled 'Development of galactose cataract in the rat, showing biomicroscopic front and slit view'). The right eye with eye drop application was assessed on the 9 grades (scores) ranging 1 to 5 at an interval of 0.5. Right eye with no abnormality observed with the slit lamp was ranked zero.

Table 6 is shown in FIG. 12.

Results (1) Ophthalmologic Examinations

Figure 4:
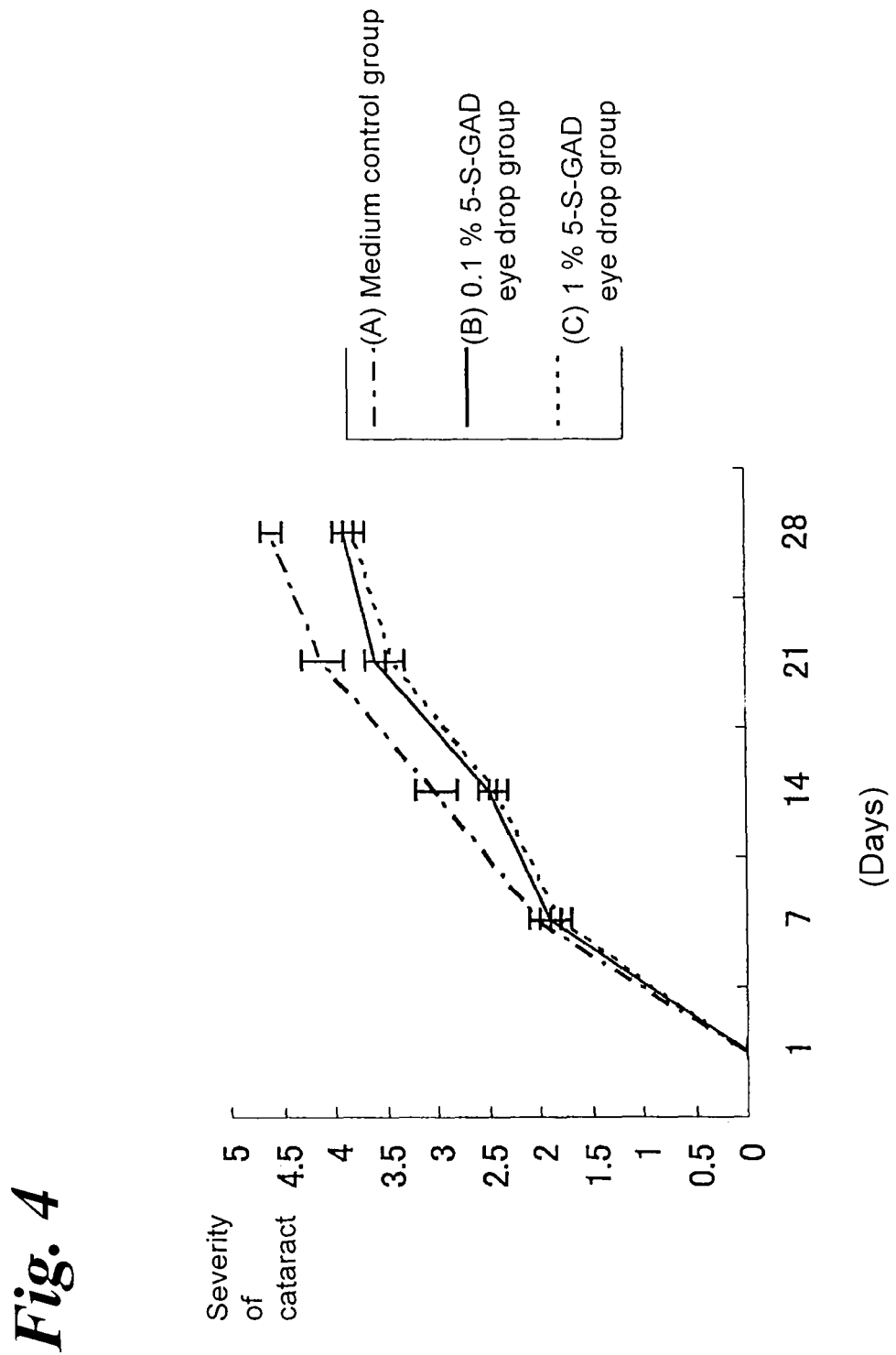
FIG. 4 A view depicting the effect of N-β-alanyl-5-S-glutathionyl-3,4-dihydroxyphenylalanine (5-S-GAD) in a galactosemic cataract model mouse.

Table 7 and FIG. 4 show the results of the observation/evaluation of the severity of cataract in the individual groups by the ophthalmologic examinations (n=10, mean±standard deviation; see Table 7 and FIG. 4.).

TABLE 7

| Groups | On day 1 | On day 7 | On day 14 | On day 21 | On day 28 |
|---|---|---|---|---|---|
| (A) | 0 ± 0 | 2.0 ± 0.1 | 3.0 ± 0.2 | 4.1 ± 0.2 | 4.6 ± 0.1 |
| (B) | 0 ± 0 | 1.9 ± 0.1 | 2.5 ± 0.1* | 3.6 ± 0.1 | 3.9 ± 0.1** |
| (C) | 0 ± 0 | 1.8 ± 0.1 | 2.4 ± 0.1* | 3.4 ± 0.1* | 3.8 ± 0.1** |

(A) The medium control group; (B) the 0.1% 5-S-GAD eye drop group; (C) the 1.0% 5-S-GAD eye drop group. Significant difference between each group and the medium control group was tested by the Wilcoxon's test (*: $p<0.05$; **: $p<0.01$).

In the medium control group, sugar cataract was never observed in any of the 10 rats on day 1; on day 7, sugar cataract at a mild level was observed in all the 10 rats (with scores of 1.5 to 2.5). On day 14, sugar cataract progressed from the mild level to a medium level (with scores of 3.0 to 4.5), while on day 21, sugar cataract at a severe level (with a score of 5.0) was observed in 2 of the 10 rats, while the remaining 8 rats were at a medium level. On day 28, 4 of the 10 rats were afflicted with sugar cataract at a severe level, while the remaining 6 rats were at a medium level. Following the prolongation of the eye dropping day period, namely the feeding day period with the galactose feed, the severity of sugar cataract progressed.

In the 0.1% 5-S-GAD eye drop group, some cases with sugar cataract at a medium level emerged on day 21 of eye dropping and thereafter. However, no case with severe sugar cataract occurred until day 28 of eye dropping. Compared with the medium control group, the scores were small values on day 14 and thereafter. Significant difference was observed among the scores on day 14 (p=0.039) and on day 28 (p=0.002).

In the 1.0% 5-S-GAD eye drop group, those observed in the 0.1% 5-S-GAD eye drop group were also observed. No case with severe sugar cataract emerged until day 28 of eye dropping. Compared with the medium control group, the scores were small values on day 14 and thereafter. Significant difference was observed among the scores on day 7 (p=0.017), on day 14 (p=0.012) and on day 28 (p=0.001).

The mean score in the 1.0% 5-S-GAD eye drop group was smaller on day 7 of eye dropping and thereafter, compared with the scores in the 0.1% 5-S-GAD eye drop group. In any of the cases in the medium control group, the 0.1% 5-S-GAD eye drop group and the 1.0% 5-S-GAD eye drop group, no abnormality of their general states was observed before eye dropping and about one hour after the last eye dropping during the eye dropping period.

(2) Pathological Analysis

Eye balls were resected on the last day (28 days later) from the galactosemic cataract models, to analyze the pathological findings.

TABLE 8

Results of pathological analysis of cataract model rats

| Pathological findings of lens | Animal groups | | |
|---|---|---|---|
| | (A) | (B) | (C) |
| Cataract | 3+ | 2+ | 2+ |
| Vacuolation of lens epithelium | + | ± | − |
| Alignment irregularity of lens cortical fiber | 2+ | + | + |
| Vacuole structure in outer cortex | 3+ | ± | ± |

(A) The medium control group; (B) the 0.1% 5-S-GAD eye drop group; (C) the 1.0% 5-S-GAD eye drop group. Pathological findings of lens: −: no change; ±: very slight change; +: slight change; 2+: medium change; 3+: significant change.

As apparently shown in the pathological findings, N-β-alanyl-5-S-glutathionyl-3,4-dihydroxyphenylalanine (5-S-GAD) exerted an apparent ameliorating effect pathologically in the galactosemic rat cataract model.

Example 5

DPPH-Scavenging Activity

5-S-GAD or TEMPOL was added to an ethanol solution of 60 µM DPPH to a final concentration of 1 to 1000 µM, for reaction at ambient temperature for 5 minutes. Subsequently, the concentration of the DPPH radical was measured via the absorbance at 517 nm. The DPPH radical concentration in a reaction solution to which PBS(−) instead of the test substance was added, was used as a control. In the same manner as in Example 2, the scavenging ratio (%) of the DPPH radical was calculated and defined as the radical-scavenging activity (see FIG. 5).

Figure 5:
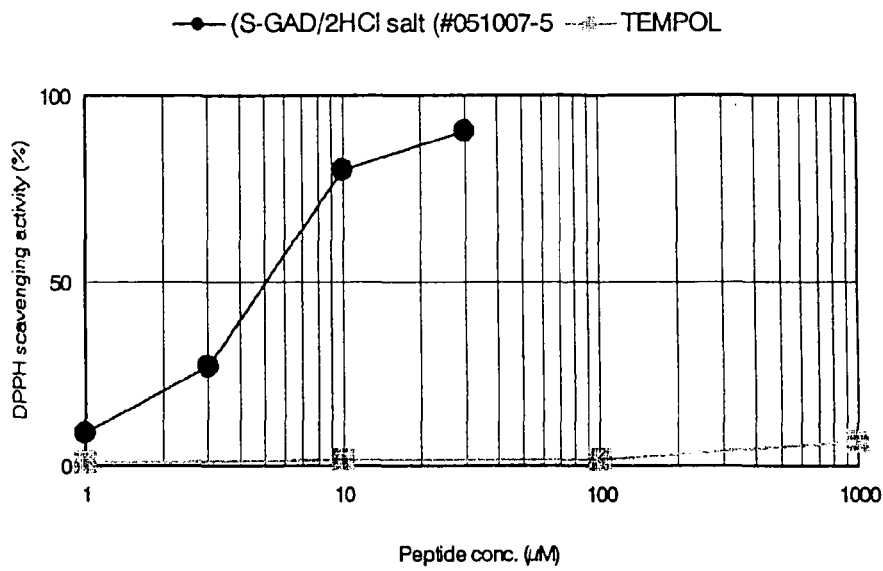
FIG. 5 A view depicting the comparison in the DPPH radical-scavenging activity between N-β-alanyl-5-S-glutathionyl-3,4-dihydroxyphenylalanine (5-S-GAD) and a control compound.

As shown in FIG. 5, N-β-alanyl-5-S-glutathionyl-3,4-dihydroxyphenylalanine (5-S-GAD) exerted an excellent DPPH radical-scavenging action compared with TEMPOL.

Example 6

DPPH-Scavenging Activity

5-S-GAD or N-acetyl-L-carnosine was added to an ethanol solution of 60 µM DPPH for reaction at ambient temperature for 5 minutes. Subsequently, the concentration of the DPPH radical was measured via the absorbance at 517 nm. The DPPH radical concentration in a reaction solution to which distilled water instead of the test substance solution was added, was used as a control. In the same manner as in Example 2, the scavenging ratio (%) of the DPPH radical was calculated and defined as the radical-scavenging activity (see FIG. 6).

Figure 6:
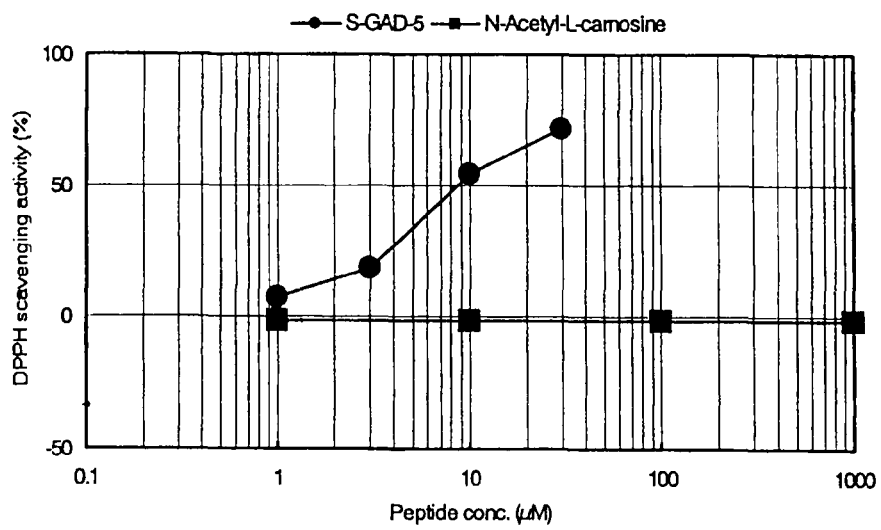
FIG. 6 A view depicting the comparison in the DPPH radical-scavenging activity between N-β-alanyl-5-S-glutathionyl-3,4-dihydroxyphenylalanine (5-S-GAD) and a control compound.

As shown in FIG. 6, N-β-alanyl-5-S-glutathionyl-3,4-dihydroxyphenylalanine (5-S-GAD) exerted an excellent DPPH radical-scavenging action compared with N-acetyl-L-carnosine.

Example 7

Superoxide Anion ($O^{2-}$)-Scavenging Activity

In a 50 mM carbonate buffer (pH 10) containing 200 µM lucigenin, 100 µM xanthine and 1 mU/mL xanthine oxidase reacted together. The chemiluminescence level depending on the generated superoxide anion ($O^{2-}$) was assayed for 10 minutes. The area under the curve indicating the total chemiluminescence over the 10 minutes was calculated. A group to which PBS(−) instead of the test substance solution was added at the same amount as that of the solution, was defined as a control. In the same manner as in Example 3, the effect of 5-S-GAD or N-acetyl-L-carnosine added on the increase of chemiluminescence was examined. The suppressive activity thereof was defined as superoxide anion-scavenging activity (%) (see FIG. 7).

Figure 7:
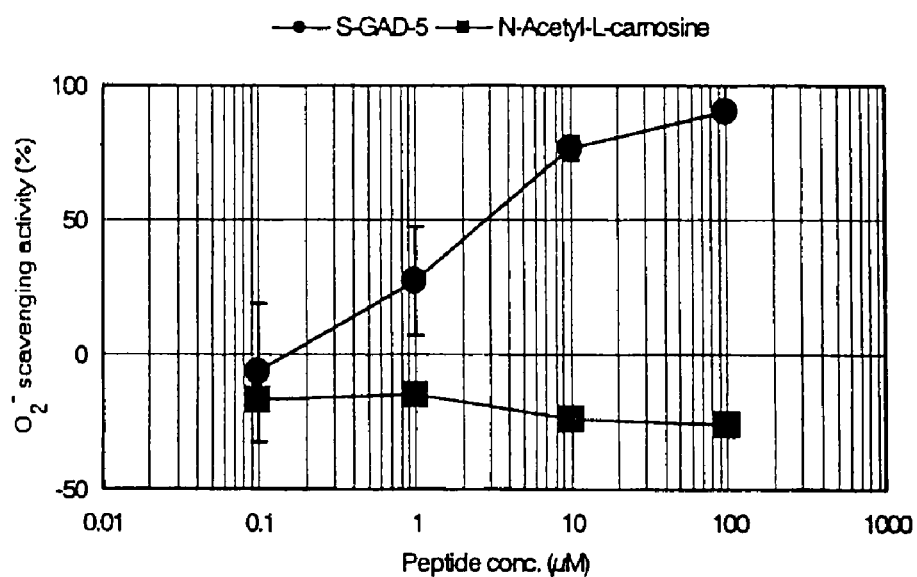
FIG. 7 A view depicting the comparison in the $O^{2-}$-scavenging activity between N-β-alanyl-5-S-glutathionyl-3,4-dihydroxyphenylalanine (5-S-GAD) and a control compound.

As shown in FIG. 7, N-β-alanyl-5-S-glutathionyl-3,4-dihydroxyphenylalanine (5-S-GAD) exerted an excellent superoxide anion ($O^{2-}$)-scavenging action compared with N-acetyl-L-carnosine.

Example 8

Superoxide Anion ($O^{2-}$)-Scavenging Activity

In a 50 mM phosphate buffer (pH 7.8), 500 µM xanthine and 75 mU/mL xanthine oxidase reacted together. The generated superoxide anion ($O^{2-}$) was assayed with a spin trapping agent (DMPO) by the electron spin resonance method (ESR). The resulting signal intensity (I) was normalized with the signal intensity of the inner standard manganese (S). The resulting value was determined as the relative intensity (RI), for comparison between the value in case of the addition of the test substance and the value in case of the addition of PBS. The ESR was measured under the following conditions. MicroWave Powder: 8 mW; Field: 335±5 mT; Scan Time: 2 min; Mod.: 0.1 mT; Amplitude:×125-400; Time Constant: 0.03 sec.

Figure 8:
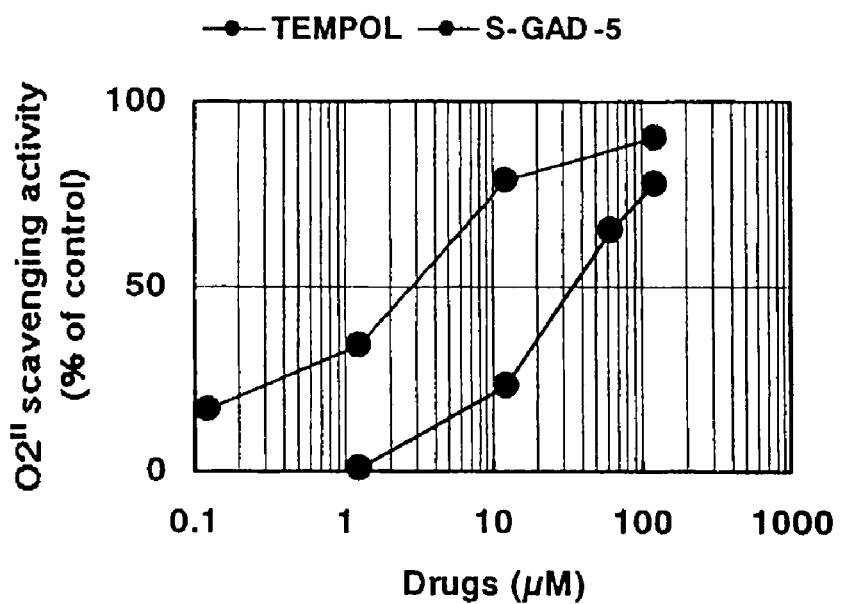
FIG. 8 A view depicting the comparison in the $O^{2-}$-scavenging activity between N-β-alanyl-5-S-glutathionyl-3,4-dihydroxyphenylalanine (5-S-GAD) and a control compound.

As shown in FIG. 8, N-β-alanyl-5-S-glutathionyl-3,4-dihydroxyphenylalanine (5-S-GAD) exerted an excellent superoxide anion ($O^{2-}$)-scavenging action compared with TEMPOL.

Example 9

Vascularization-Suppressing Action

5-S-GAD was added to a matrigelplug containing 100 ng/mL VEGF, for injections into female C57BL/6 mice. 6 days later, the matrigel plug was scissored out, to assay the hemoglobin content in the matrigel. The results are shown in mean±standard deviation. Testing were done by the Student's t test (*P<0.05).

Figure 9:
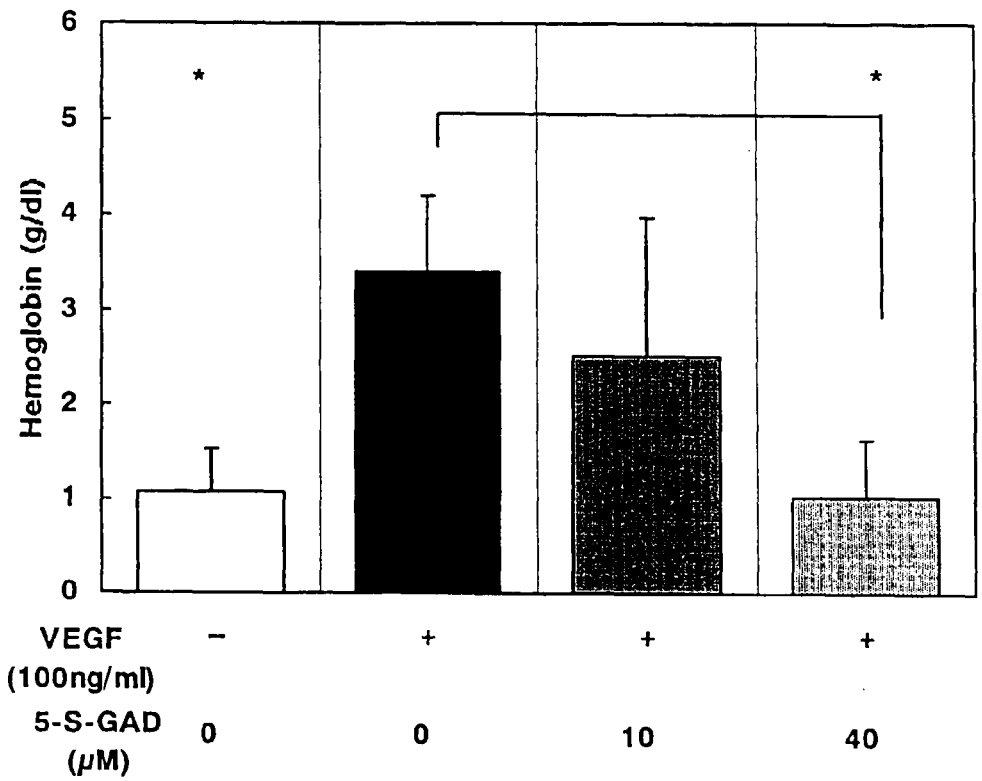
FIG. 9 A view depicting in the action of suppressing vascularization induced by VEGF in N-β-alanyl-5-S-glutathionyl-3,4-dihydroxyphenylalanine (5-S-GAD).

As shown in FIG. 9, 5-S-GAD at 40 µM suppressed significantly the VEGF-triggered vascularization (P<0.05).

Example 10

Vascularization-Suppressing Action

A ring of a 3-mm diameter was placed on a chicken egg chorioallantois on day 5 after oviposition. 10 µL of the test substance diluted with 1% methylcellulose was added inside the ring. After incubation at 37° C. for 48 hours, fat emulsion was injected into the chorioallantois. A part from which the ring was displaced was photographed. Using an image analysis software (Kurabo Industries, Ltd.), the vascular area was measured.

Figure 10:
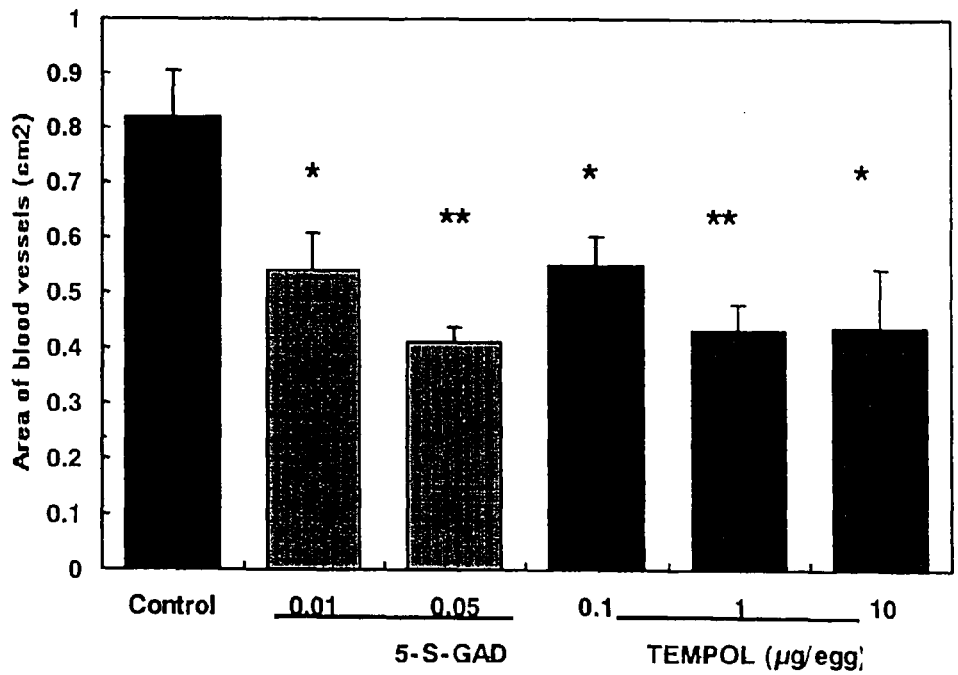
FIG. 10 A view depicting the comparison in the action of suppressing vascularization between N-β-alanyl-5-S-glutathionyl-3,4-dihydroxyphenylalanine (5-S-GAD) and control compounds.

As shown in FIG. 10, 5-S-GAD suppressed vascularization significantly (* P<0.05; ** P<0.01).

Example 11

Effect on the Oxidation of LDL in Human Blood

LDL was prepared by a fractionation and centrifugation method. A fraction at a specific gravity of 1.019 to 1.063 g/mL in serum was defined as human LDL. 5 µM $CuSO_4$, 5-S-GAD (3 to 100 µM) and N-acetyl-carnosine (100 µM to 10 mM) or L-carnosine (10 µM to 10 mM) were added to 0.2 mg/mL LDL, for incubation at 37° C. for 3 hours. After termination of the incubation, TEARS (a substance reactive with thiobarbituric acid) was assayed. Although the TBA reaction is a non-specific reaction, the reaction is used for a method of assaying various lipid peroxide products including malone dialdehyde. An experiment of peroxidation with copper sulfate was done twice (N=2).

An aqueous solution containing 3.75 mg/mL thiobarbituric acid (TBA), 150 mg/mL trichloroacetic acid (TCA) and 0.25 N hydrochloric acid (HCl) was prepared as the TBA reagent, while standard solutions (2, 5, 10, 20, 40 µM) of tetramethoxypropane were prepared. 100 µL each of an LDL sample or a standard solution was added together with 200 µL of the TBA reagent into an Eppendorf tube (1.5 mL), which was then sealed with a cap for thorough mixing. After the resulting mixture was heated at 95° C. for 15 minutes, the mixture was cooled in water and centrifuged at 3000 rpm for 5 minutes. The supernatant was assayed of the absorbance (535 nm). Based on the absorbance of the standard solution, a standard curve was prepared. Based on the standard curve, the amount of TBARS in the LDL sample was calculated (in nmol/mg LDL protein) (see FIG. 11).

Figure 11:
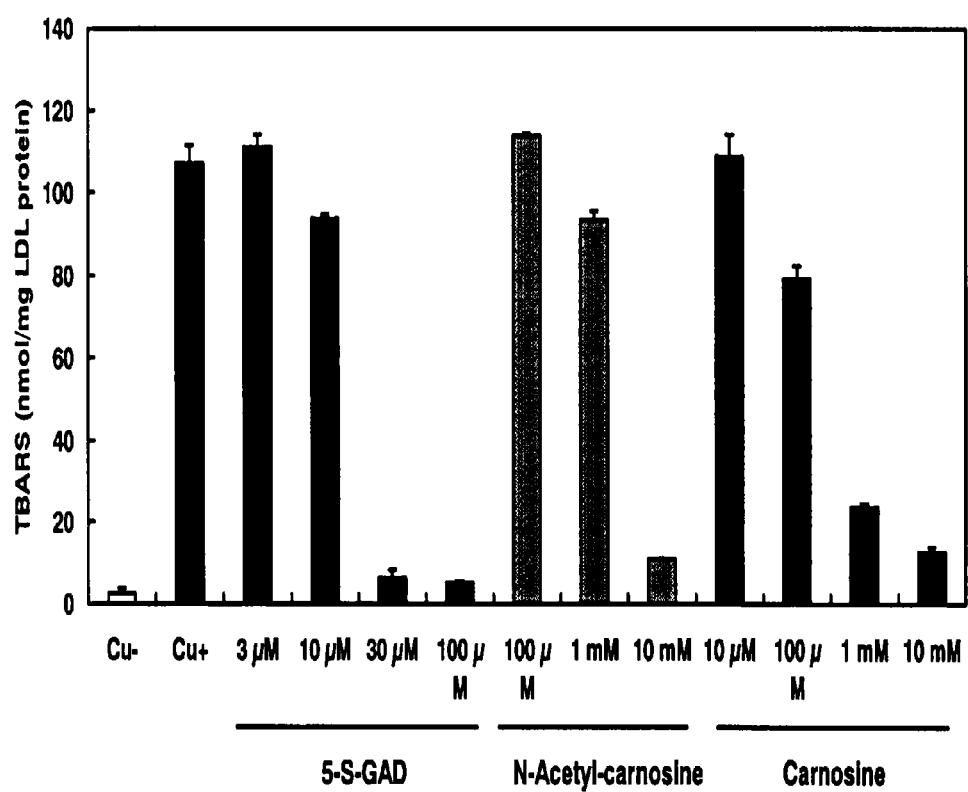
FIG. 11 A view depicting the comparison in the anti-oxidation action between N-β-alanyl-5-S-glutathionyl-3,4-dihydroxyphenylalanine (5-S-GAD) and control compounds.

As shown in FIG. 11, N-β-alanyl-5-S-glutathionyl-3,4-dihydroxyphenylalanine (5-S-GAD) exerted an excellent antioxidation action compared with N-acetyl-carnosine and L-carnosine.

The invention claimed is:

1. A method of and treating at least one disease or condition selected from the group consisting of cataracts; damage to the eye following ophthalmologic surgery; damage to the eye from contact lenses; damage following a corneal transplantation; open-angle glaucoma, corneal disease; dry eye; bleary eye; macular degeneration; age-related macular degeneration; retinopathy of prematurity; eye siderosis; and uveal disease in a subject in need thereof, the method comprising administering an effective amount of an opthalmically suitable composition comprising a 3,4-hydrophenylalanine compound of formula (I) to the eye of the subject:

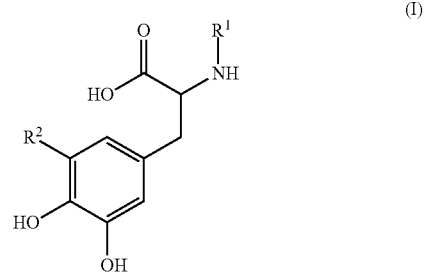

(I)

wherein $R^1$ represents hydrogen atom or an a-amino acid, a β-amino acid, or a γy-amino acid bound via an amide bond;

$R^2$ represents hydrogen atom or a group represented by the following formula (II):

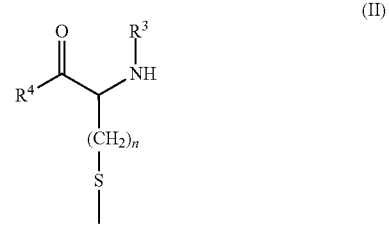

(II)

wherein $R^3$ represents an α-amino acid, a β-amino acid, or a γ-amino acid;

$R^4$ represents hydroxyl group an α-amino acid, a β-amino acid, or a γ-amino acid; and n represents 1 or 2;

wherein if either $R^1$ or $R^2$ is hydrogen atom, the other is not a hydrogen atom, or a pharmaceutically acceptable salt thereof.

2. The method according to claim 1, where the 3,4-dihydroxyphenylalanine compound is N-β-alanyl-5-S-glutathionyl-3,4-dihydroxyphenylalanine.

3. The method according to claim 1, wherein $R^1$ is a β-alanine residue.

4. The method according to claim 1, wherein $R^3$ is a glutamic acid residue.

5. The method according to claim 1, wherein $R^4$ is a glycine residue.

6. The method according to claim 1, wherein n is 1.

7. The method of claim 1, wherein the disease or condition is cataracts.

8. The method of claim 1, wherein the disease or condition is damage to the eye following ophthalmologic surgery.

9. The method of claim 1, wherein the disease or condition is damage to the eye from contact lenses.

10. The method of claim 1, wherein the disease or condition is damage following a corneal transplantation.

11. The method of claim 1, wherein the disease or condition is open-angle glaucoma.

12. The method of claim 1, wherein the disease or condition is corneal disease.

13. The method of claim 1, wherein the disease or condition is dry eye.

14. The method of claim 1, wherein the disease or condition is bleary eye.

15. The method of claim 1, wherein the disease or condition is macular degeneration.

16. The method of claim 1, wherein the disease or condition is age-related macular degeneration.

17. The method of claim 1, wherein the disease or condition is retinopathy of prematurity.

18. The method of claim 1, wherein the disease or condition is eye siderosis.

19. The method of claim 1, wherein the disease or condition is uveal disease.

* * * * *